United States Patent [19]
Krüger et al.

[11] Patent Number: 5,348,958
[45] Date of Patent: Sep. 20, 1994

[54] HETARYLOXY-β-CARBOLINES, AND USE AS PHARMACEUTICAL AGENTS FOR TREATING EPILEPSY AND ANXIETY

[75] Inventors: Martin Krüger; Andreas Huth; Dieter Seidelmann; Herbert Schneider; Lechoslaw Turski; David N. Stephens, all of Berlin, Fed. Rep. of Germany

[73] Assignee: Schering Aktiengesellschaft, Berlin and Bergkamen, Fed. Rep. of Germany

[21] Appl. No.: 892,819

[22] Filed: Jun. 5, 1992

[30] Foreign Application Priority Data

Jun. 5, 1991 [DE] Fed. Rep. of Germany ....... 4118741

[51] Int. Cl.$^5$ .................. C07D 471/04; C07D 417/12; A61K 31/44; A61K 31/495
[52] U.S. Cl. ..................... 514/249; 514/292; 546/86; 544/354
[58] Field of Search ............ 546/86; 514/292, 249; 544/353, 354

[56] References Cited

U.S. PATENT DOCUMENTS

| | | | |
|---|---|---|---|
| 4,877,792 | 10/1989 | Biere et al. | 514/292 |
| 4,933,345 | 6/1990 | Huth et al. | 514/253 |
| 4,960,777 | 10/1990 | Biere et al. | 514/253 |

FOREIGN PATENT DOCUMENTS

| | | | |
|---|---|---|---|
| 0237467 | 9/1987 | European Pat. Off. | 546/86 |
| 0305322 | 3/1989 | European Pat. Off. | 544/405 |

OTHER PUBLICATIONS

Chemical Abstracts, vol. 107 (No. 21) Abst. No. 107:198,295-U. Nov. 23, 1987.

Primary Examiner—Alan L. Rotman
Attorney, Agent, or Firm—Millen, White, Zelano & Branigan

[57] ABSTRACT

Hetaryloxy-β-carbolines of formula I

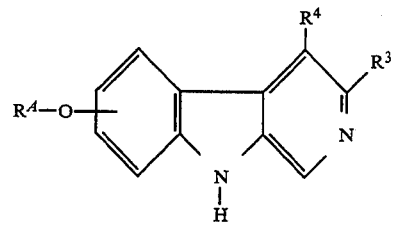

in which
$R^4$ means a benzocondensed hetaryl radical with 1–2 nitrogen atoms optionally substituted with halogen, $C_{1-6}$ alkyl, $C_{1-6}$ alkoxy, $C_{1-6}$ alkylthio, trifluoromethyl or $SO_2$—$R^1$ or a 5- or 6-membered hetaryl radical with 1–2 nitrogen atoms substituted with halogen, $C_{1-6}$ alkyl, $C_{1-6}$ alkoxy, $C_{1-6}$ alkylthio, trifluoromethyl or $SO_2$—$R^1$ are useful pharmaceutical agents.

6 Claims, No Drawings

HETARYLOXY-β-CARBOLINES, AND USE AS PHARMACEUTICAL AGENTS FOR TREATING EPILEPSY AND ANXIETY

SUMMARY OF THE INVENTION

The invention relates to new hetaryloxy-β-carboline derivatives, their production and use in pharmaceutical agents.

In EP-A-237 467 and EP-A-305 322, β-carbolines substituted with a hetaryloxy radical are described, which influence the central nervous system and are used as psychopharmaceutical agents. According to these patent applications, it was not to be expected that with the introduction of the hetaryl substituents according to the invention, a displacement of the active profile of the compounds takes place and that the compounds show an improved side effect profile because of the absent muscular relaxation.

The compounds according to the invention have formula I

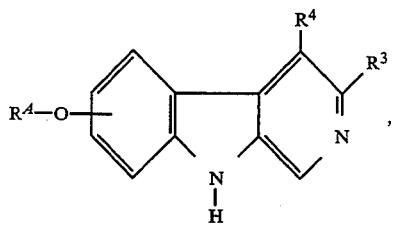

in which $R^4$ means a triazine or benzocondensed hetaryl radical with 1–2 nitrogen atoms optionally substituted with halogen, $C_{1-6}$ alkyl, $C_{1-6}$ alkoxy, $C_{1-6}$ alkylthio, trifluoromethyl or $SO_2$—$R^1$ or represents a 5- or 6-membered hetaryl radical with 1–2 nitrogen atoms substituted with halogen, $C_{1-6}$ alkyl, $C_{1-6}$ alkoxy, $C_{1-6}$ alkylthio, trifluoromethyl or —$SO_2$—$R^1$, and $R^1$ is $C_{1-4}$ alkyl or phenyl optionally substituted 1–2 times with $C_{1-4}$ alkyl and $R^4$ can be substituted once to twice, and the substituent is not halogen, if $R^4$ means pyridine, $R^4$ means hydrogen, $C_{1-6}$ alkyl, $C_{1-6}$ alkoxy-$C_{1-2}$ alkyl and $R^3$ means —$CO_2$13 $C_{1-6}$ alkyl, —CO—$R^2$, —$CO_2H$,

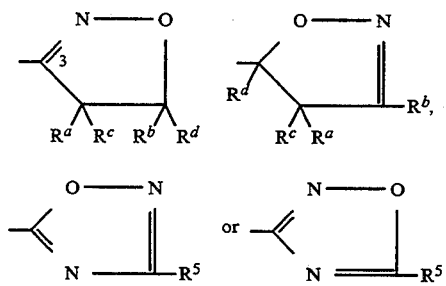

and $R^2$ means $C_{1-4}$ alkyl, $C_{3-7}$ cycloalkyl, $C_{7-9}$ bicycloalkyl or a monocyclic or bicyclic $C_{6-12}$ aryl radical optionally substituted with $C_{1-4}$ alkyl, $C_{1-4}$ alkoxy or amino, $R^a$ and $R^b$ are the same or different and respectively mean hydrogen, $C_{1-6}$ alkoxy, $C_{1-6}$ alkyl, —$CH_2$—O—$C_{1-4}$ alkyl, phenyl or benzyl, $R^c$ and $R^d$ respectively mean hydrogen or together a bond and $R^5$ is hydrogen, $C_{1-4}$ alkyl or $C_{3-9}$ cycloalkyl, as well as their isomers and acid addition salts. Substituent $R^4$ can be in position 5–8 of the A-ring, preferably in 5-, 6- or 7-position. Alkyl portions are both straight-chain and branched-chain radicals, such as, for example, methyl, ethyl, propyl, isopropyl, butyl, isobutyl, sec-butyl, tert-butyl, pentyl, isopentyl and hexyl.

Halogens are fluorine, chlorine, bromine and iodine.

Cycloalkyl groups are, for example, cyclopropyl, cyclobutyl, cyclopentyl, cyclohexyl or cycloheptyl.

As benzocondensed hetaryl radicals with 1–2 nitrogen atoms, there are, for example, quinoline, isoquinoline, quinoxaline, benzimidazo. Generally, these have 2 rings each of which can be a 4-, 5- or 6-membered ring, there being generally about 8–12 ring atoms in total.

Substituted nitrogen-containing hetaryl radicals, for example, include pyridine, pyrimidine, pyrazine, pyridazine, imidazole, etc.

Suitable bicycloalkyl radicals $R^2$ are bicycloheptyl and bicyclooctyl. Suitable monocyclic or bicyclic aryl radicals $R^2$ are, for example, phenyl, biphenyl, naphthyl and indenyl.

The number of substituents on the hetaryl radicals $R^4$, on phenyl radical $R^1$ and on aryl radical $R^2$ can be one or two and can be in any position.

Preferred embodiments for $R^4$ include quinoline, isoquinoline or quinoxaline each optionally substituted with halogen, $C_{1-6}$ alkyl or $C_{1-6}$ alkoxy, triazine optionally substituted once to twice with halogen, $C_{1-6}$ alkyl, $C_{1-6}$ alkoxy or $C_{1-6}$ alkylthio or pyridine, pyrimidine, pyrazine or pyridazine radicals each substituted with $C_{1-6}$ alkyl, $C_{1-6}$ alkoxy, $C_{1-6}$ alkylthio, trifluoromethyl or $SO_2$—$R^1$, or pyrimidine, pyridazine or pyrazine each substituted with halogen.

For $R^3$, —$CO_2$-$C_{1-6}$ alkyl, —CO—$R^2$ wherein $R^2$ is a $C_{3-7}$ cycloalkyl or an optionally substituted phenyl radical or isoxazol-3-yl radical are preferred.

The physiologically compatible acid addition salts are derived from the known inorganic and organic acids, such as, for example, hydrochloric acid, hydrobromic acid, sulfuric acid, phosphoric acid, formic acid, acetic acid, benzoic acid, maleic acid, fumaric acid, succinic acid, tartaric acid, citric acid, oxalic acid, glyoxylic acid as well as from alkanesulfonic acids, such as, for example, methanesulfonic acid, ethanesulfonic acid, benzenesulfonic acid, p-toluenesulfonic acid, among others.

The compounds of formula I as well as their acid addition salts can be used as pharmaceutical agents because of their affinity to benzodiazepine receptors They have a partial agonistic effect on the properties known for the benzodiazepines, which is characterized in that the compounds, for example, have an anticonvulsive and anxiolytic effect and are not atactic/muscle-relaxing. To test the anxiolytic effect, the compounds can be tested in the 4-plate test according to the method of Boissier et al., Eur. J. Pharmacol. 4, 145–150 (1968). In the table, the minimal effective dose (MED) is indicated, which increases the locomotor activity of the afflicted mice after i.p. treatment.

TABLE

| Compound | MED mg/kg i.p. |
|---|---|
| A | 1.56 |
| B | 0.39 |

A = 6-(1-isoquinolyloxy)-4-methoxymethyl-β-carboline-3-carboxylic acid-isopropyl ester
B = 6-(2,6-dimethoxy-4-pyrimidinyloxy)-4-methoxymethyl-β-carboline-3-carboxylic acid-isopropyl ester Because of the good effectiveness in the PTZ convulsion test and in the 4-plate test, the compounds according to the invention are suitable especially for treatment of epilepsy and anxiety.

To use the compounds according to the invention as pharmaceutical agents, the latter are brought into the form of a pharmaceutical preparation, which in addition to the active ingredient for enteral or parenteral administration contains suitable pharmaceutical, organic or inorganic inert vehicles, such as, for example, water, gelatin, gum arabic, lactose, starch, magnesium stearate, talc, vegetable oils, polyalkylene glycols, etc.

The pharmaceutical preparations can be present in solid form, for example, as tablets, coated tablets, suppositories, capsules or in liquid form, for example, as solutions, suspensions or emulsions. They further optionally contain auxiliary agents such as preservatives, stabilizers, wetting agents or emulsifiers, salts to change the osmotic pressure or buffers.

For parenteral use, especially injection solutions or suspensions, especially aqueous solutions of the active compounds in polyhydroxyethoxylated castor oil, are suitable.

As vehicle systems, surface-active auxiliary agents such as salts of bile acids or animal or vegetable phospholipids but also their mixtures as well as liposomes or their components can also be used.

For oral use, tablets, coated tablets or capsules with talc and/or hydrocarbon vehicles or binding agents, such as, for example, lactose, corn or potato starch, are especially suitable. The use can also take place in liquid form, such as, for example, as juice, to which a sweetener optionally is added.

The compounds according to the invention can be used in a dosage unit of 0.05 to 100 mg of active substance in a physiologically compatible vehicle.

The compounds according to the invention are generally used in a dose of 0.1 to 300 mg/day, preferably 0.1 to 30 mg/day, especially preferably 1–20 mg/day, for example as anxiolytic agents analogous to diazepam.

The production of the compounds according to the invention takes place according to methods known in the art. For example, compounds of formula I are attained in that a) compounds of formula II

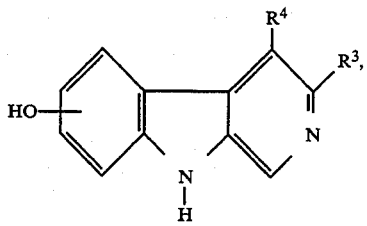

in which $R^4$ and $R^3$ have the above-named meaning, with $R^A$ Y, in which $R^A$ has the above-named meaning and Y is halogen or a reactive group, are etherified or b) compounds of formula III

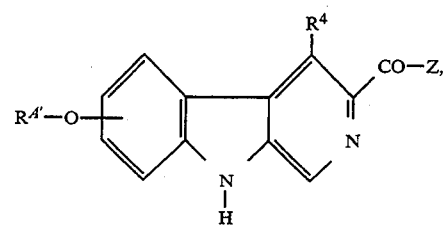

in which $R^4$ has the above-named meaning, $R^{A'}$ is hydrogen or $R^A$ and Z is hydrogen, $C_{1-4}$ alkoxy or a reactive acid derivative, are reacted with a lithium-organic compound, optionally after introducing a protecting group in 9-position to compounds of formula I with $R^3 = -CO-R^2$ or c) compounds of formula IV

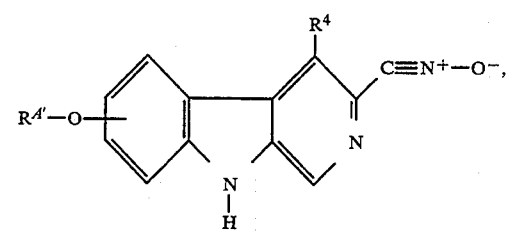

in which $R^{A'}$ is hydrogen or $R^A$ and $R^4$ has the above-named meaning, are cyclized with a compound of formula V

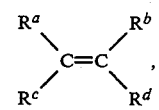

in which $R^a$, $R^b$, $R^c$, and $R^d$ have the above-named meaning, to compounds of formula I with $R^3$ meaning

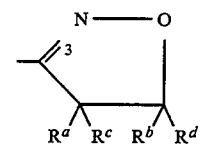

or d) compounds of formula VI

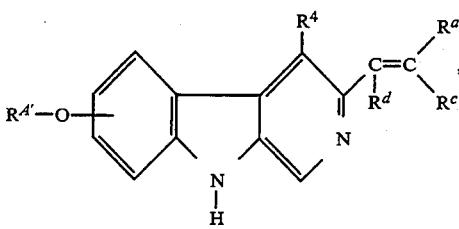

in which $R^{A'}$ is hydrogen or $R^A$ and $R^4$, $R^a$, $R^c$ and $R^d$ have the above-named meaning, are cyclized with a nitrile oxide of formula VII

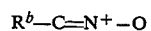

in which $R^b$ has the above-named meaning, to compounds of

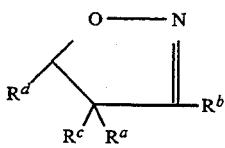

VII or e) compounds of formula VIII

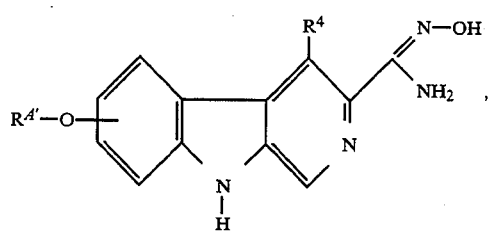

VIII in which $R^{A'}$ is hydrogen or $R^A$ and $R^4$ has the above-named meaning, are cyclized with a compound of formula $(R^5CO)_2O$ with $R^5$ in the above-named meaning to compounds with $R^3$ meaning

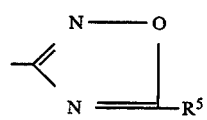

or f) compounds of formula IX

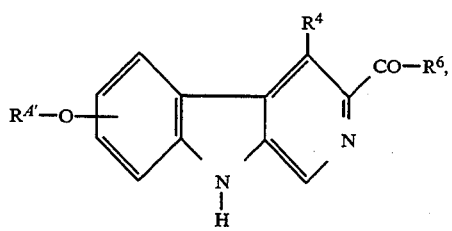

IX in which $R^{A'}$ is hydrogen or $R^A$, $R^4$ above-named meaning and $R^6$ means OH or a reactive acid derivative, are reacted with a compound of formula

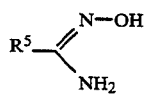

to compounds with $R^3$ meaning

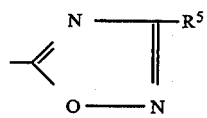

and then optionally protecting groups are cleaved off or interesterified or the ester group is hydrolyzed or acid addition salts are formed or isomers are separated.

The introduction of substituent $R^A$ according to process variant a) takes place according to the usual methods of etherification, which are described, for example, in EP-A-237 467.

Reactive compound $R^A$—Y, in which Y means, for example, halogen, tosylate, mesylate or triflate, is reacted in the presence of a base such as alkaline-earth or alkali-alcoholate or -hydroxide, alkali or alkaline-earth carbonate in polar solvents, such as dimethylsulfoxide, dimethylformamide, acetonitrile or alcohols at room temperature or increased temperature, optionally in the presence of phase transfer catalysts.

The introduction of substituent $R^3$ meaning —CO—$R^2$ according to process variant b) takes place according to the methods described in WO 91/09858. For example, a β-carboline-3-carboxylic acid-alkyl ester derivative or its reactive acid derivative, such as carboxylic acid imidazolide, is reacted with a lithium-organic compound $R^2Li$ in aprotic polar solvents, such as cyclic or acyclic ethers or hydrocarbons at temperatures of −70° C. up to room temperature. Suitably, a protecting group can be present in 9-position of the β-carboline such as tosyl, mesyl or a trialkylsilyl group, which is cleaved off in the working up of the reaction mixture or thereafter in the usual way depending on the type of protecting group.

The cycloaddition of compounds of formulas IV and VI according to processes c) and d) takes place according to the methods described in EP-A-305 322. The addition is performed at temperatures of 0° C. -40° C. in an aprotic solvent, such as aliphatic or cyclic ethers, halogenated hydrocarbons, dimethylformamide, i.a. β-Carboline derivatives protected in 9-position optionally can be used in the reaction. The protecting group is cleaved off in the usual way with the working up of the reaction mixture or thereafter by treatment with bases or acids depending on the type of protecting group.

The production of the nitrile oxides takes place, for example, by reaction of β-carboline-3-carbaldehydes to the corresponding oximes, which can be converted, for example, with N-halogen-succinimide, tert-butoxychlorite or Na-hypochlorite in the above-mentioned aprotic solvents to hydroxamic acid halides. With bases such as Na- or K-alcoholates, trialkylamines, Hünig base, DBU or diazabicyclooctane, hydrogen halide is cleaved off from the hydroxamic acid halides and nitrile oxides are obtained, which are subjected to the cycloaddition without isolation (R. Annunziata et al., J. Chem. Soc. 1987, 529).

The introduction of the oxadiazole radicals according to process variants e) and f) can take place according to the methods described in EP-161 574. The production of 1,2,4-oxadiazol-3-yl-carbolines takes place, for example, by reaction of β-carboline-3-carboxamide-carboxamide oximes with acid anhydrides $(R^5CO)_2O$ at room temperature up to boiling temperature of the mixture.

To introduce the 1,2,4-oxadiazol-5-yl radical, the β-carboline-3-carboxylic acid or its reactive acid derivative, such as halide, imidazolide or mixed anhydride or carboxylic acid alkyl ester is reacted in the presence of alcoholate with an amide oxime

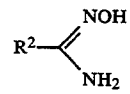

in aprotic solvents such as hydrocarbons, such as toluene, ethers or dimethylformamide at room temperature or increased temperature.

If an interesterification is desired, the methods described in EP-A-237 467 can be used by being interesterified with alkali alcoholates or the corresponding alcohol, optionally by adding titanium-tetra-isopropylate as catalyst at increased temperature. The introduction of the tert-butyl ester group takes place, e.g., by reaction of carboxylic acid with tert-butoxy-bis-dimethyl-aminomehtane. The hydrolysis of the ester group can take place as acid or alkaline in the usual way, for example, with Na- or K-hydroxide in protic solvents or according to the processes described in EP-A-161 574.

The mixtures of isomers can be separated according to the usual methods such as, for example, crystallization, chromatography or salt formation in the diastereomers or enantiomers.

For the formation of physiologically compatible acid addition salts, a compound of formula I is dissolved, for example, in a little alcohol and mixed with a concentrated solution of the desired acid.

Insofar as the production of the initial compounds is not described, the latter are known or can be produced analogously to known compounds or processes described here from known or routinely preparable starting materials.

For example, the production of 3-carboxylic acid esters of formula II is described in EP-A-130 140.

Without further elaboration, it is believed that one skilled in the art can, using the preceding description, utilize the present invention to its fullest extent. The following preferred specific embodiments are, therefore, limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 41 18 741.5, filed Jun. 5, 1991, are hereby incorporated by reference.

EXAMPLES

Example 1

6-(1-Isoquinolyloxy)-4-methoxymethyl-β-carboline-3carboxylic acid isopropyl ester 1.3 g of potassium hydroxide powder is added to 25 ml of dimethyl sulfoxide at room temperature. Then, 3.14 g of 6-hydroxy-β-carboline-3-carboxylic acid isopropyl ester is added in portions to the batch and then a solution of 2 g of 1-chloroisoquinoline in 2 ml of dimethyl sulfoxide is instilled. After 3 hours of heating to a bath temperature of 90°-95° C, 375 mg of 1-chloroisoquinoline is added once more and heated for 2 hours to 100° C. It is poured on ice, adjusted to pH 5 with glacial acetic acid, the precipitate is suctioned off and rewashed with ethyl acetate. This residue is chromatographed on silica gel with methylene chloride:ethanol =13:1 as eluant. After concentration by evaporation of the correspondingly combined fractions and recrystallization, 2.5 g (55% of theory) of 6-(1-isoquinolyloxy)-4-methoxymehtyl-β-carboline-3-carboxylic acid isopropyl ester of melting point 10° C. is obtained.

In an analogous way, there are produced:
6-(4-Quinolyloxy)-4-methoxymethyl-β-carboline-3carboxylic acid isopropyl ester, melting point 165°-167° C.

6-(4-methyl-2-quinolyloxy)-4-methoxymethyl-β-carboline-3-carboxylic acid isopropyl ester, melting point 174°-176° C.

6-(2-quinolyloxy)-4-methoxymethyl-β-carboline-3-carboxylic acid isopropyl ester, melting point 10° C.

6-(3-chloro-2-quinoxalyloxy)-4-methoxymethyl-β-carboline-3-carboxylic acid isopropyl ester, melting point 223°-228° C.

5-(1-isoquinolyloxy)-4-methoxymethyl-β-carboline-3carboxylic acid isopropyl ester, melting point 235°-237° C.

6-(5-tosyl-2-pyridyloxy)-4-methoxymethyl-β-carboline-3-carboxylic acid isopropyl ester, melting point 206°-207° C.

6-(2-tosyl-5-pyridyloxy)-4-methoxymethyl-β-carboline-3-carboxylic acid isopropyl ester, melting point 206°-207° C.

6-(5-bromo-2-pyrazinyloxy)-4-methoxymethyl-β-carboline-3-carboxylic acid isopropyl ester, melting point 180°-181° C.

6-(5-bromo-2-pyrazinyloxy)-4-methoxymethyl-β-carboline-3-carboxylic acid-tert-butyl ester, melting point 195°-196° C.

6-(2-methylmercapto-4-pyrimidinyloxy)-4-methoxymethyl-β-carboline-3-carboxylic acid-isopropyl ester, melting point 209°-210° C.

6-(2-methylsulfonyl-4-pyrimidinyloxy)-4-methoxymethyl-β-carboline-3-carboxylic acid-isopropyl ester, melting point 178°-179° C.

6-(5-trifluoromethyl-2-pyridyloxy)-4-methoxymethyl-β-carboline-3-carboxylic acid-isopropyl ester, melting point 215°-216° C.

6-(4,6-dimethoxy-2-pyrimidinyloxy)-4-methoxymethyl-β-carboline-3-carboxylic acid-isopropyl ester, melting point 130°-132° C.

6-(5-bromo-2-pyrimidinyloxy)-4-methoxymethyl-β-carboline-3-carboxylic acid-isopropyl ester, melting point 211°-212° C.

6-(4,6-dimethyl-2-pyrimidinyloxy)-4-methoxymethyl-β-carboline-3-carboxylic acid-isopropyl ester, melting point 84°-85° C.

6[4,6-bis(methylthio)-1,3,5-triazin-2-yloxy]-4-methoxymethyl-β-carboline-3-carboxylic acid-isopropy ester, melting point 167°-170° C.

6-(2,6-dimethoxy-4-pyrimidinyloxy)-4-methoxymethyl-β-carboline-3-carboxylic acid-isopropyl ester, point 159°-161° C.

6-(4,6-dimethoxy-1,3,5-triazin-2-yloxy)-4-methoxymethyl-β-carboline-3-carboxylic acid-isopropyl ester, melting point 159°-°162° C.

6-(1,3,5-triazin-2-yloxy)-4-methoxymethyl-β-carboline-3-carboxylic acid-isopropyl ester, melting point 168°-170° C.

6-(5-methyl-2-pyrazinyloxy)-4-methoxymethyl-β-carbo-line-3-carboxylic acid-isopropyl ester, melting point 180° C.

6-(5-methyl-2-pyrazinyloxy)-4-methoxymethyl-β-carbo-line-3-carboxylic acid-tert-butyl ester, melting point 196° C.

-(5-methyl-2-pyrazinyloxy)-3-(5-methoxymethyl-3-isoxazolyl)-4-methoxymethyl-β-carboline, melting point 196° C.

6-(5-methylpyrazine-2-yl)-oxy-4-ethyl-β-carboline-3-carboxylic acid-isopropyl ester, melting point 175°-177° C.

6-(5-bromopyrazine-2-yl)-oxy-4-ethyl-β-carboline-3-carboxylic acid-isopropyl ester, melting point 227°-228° C.

6-(5-bromopyrazine-2-yl)-oxy-4-methyl-β-carboline-3-carboxylic acid-isopropyl ester, melting point 245°–246° C.

6-(6-methoxypyridine-2-yl)-oxy-4-methoxymethyl-β-carboline-3-carboxylic acid-isopropyl ester, melting point 92°–99° C.

6-(5-chloropyridazine-2-yl)-oxy-4-methoxymethyl-β-carboline-3-carboxylic acid-isopropyl ester, melting point 223° C.

6-(5-chloropyridazine-2-yl)-oxy-4-methoxymethyl-β-carboline-3-carboxylic acid-tert-butyl ester, melting point 197° C.

6-(6-methoxypyridine-2-yl)-oxy-4-methoxymethyl-6²-carboline-3-carboxylic acid-tert-butyl ester, melting point 166° C.

6-(5-trifluoromethylpyridine-2-yl)-oxy-4-methoxymethyl-β-carboline-3-carboxylic acid-isopropyl ester, melting point 206° C.

5-(5-trifluoromethylpyridine-2-yl)-oxy-4-methoxymethyl-β-carboline-3-carboxylic acid-tert-butyl ester, melting point 178°–180° C.

EXAMPLE 2

6-(1-Isoquinolyloxy)-4-methoxymethyl-3-(5-methoxymethylisoxazol-3-yl) β-carboline 330 mg of 6-(1-isoquinolyloxy)-4-methoxymethyl-β-carboline-3-carboxylic acid isopropyl ester is mixed in 10 ml of toluene with 0.62 ml of triethylamine and 0.2 chlorotrimethylsilane and heated for 45 minutes to a bath temperature of 50°–60° C. After concentration by evaporation to about 6 ml, it is cooled to −78° C. under argon and 1.25 ml of a 1.2 molar diisobutyl aluminum hydride is instilled in hexane. After 30 minutes at −78° C., it is mixed with 3 ml of ethanol and 0.75 ml of 1N NaOH. It is mixed with ethyl acetate and very little water. The organic phase is separated and concentrated by evaporation without drying. The residue is mixed with hexane and yields 440 mg of 6-(1-isoquinolyloxy)-4-methoxymethyl-β-carboline-3-carbaldehyde. 254 mg of it is mixed in 2.5 ml of dimethylfuran with 67.5 mg of hydroxylamine hydrochloride and 69 mg of potassium hydroxide powder and allowed to stand for 16 hours at room temperature. The batch is poured on ice and the precipitate is suctioned off and rewashed with water. 133 mg of 6-(1-isoquinolyloxy-4-methoxymethyl-β-carboline-3-carbaldehyde oxime of melting point 215°–218° C. is obtained.

450 mg of this oxime is dissolved in 7 ml of dimethylformamide and stirred With 218 mg of N-bromosuccinimide for 30 minutes at room temperature. After adding 0.8 ml of triethylamine and 0.16 ml of methyl propargyl ether, it is stirred for 3 hours at room temperature. After concentration by evaporation, it is dispersed in ethyl acetate/water and the organic phase is dried, filtered and concentrated by evaporation. The residue is chromatographed twice on silica gel first with methylene chloride:ethanol =10:1 and then with methylene chloride:ethanol =12:1. After recrystallization of the corresponding fractions that are combined and concentrated by evaporation, 200 mg of 6-(1-isoquinolyloxy)-4-methoxymethyl-3-(5-methoxymethylisoxazol-3-yl)-β-carboline of melting point 107°–112° C. (ethyl acetate/hexane) is obtained.

EXAMPLE 3

6-(1-Isoquinolyloxy)-4-methoxymethyl-3-benzoyl-β-carboline 476 mg of 6-(1-isoquinolyloxy)-4-methoxymethyl-9-tosyl-β-carboline-3-carboxylic acid isopropyl ester is mixed in 10 ml of tetrahydrofuran under argon at −60° C. with 0.79 ml of a 0.9 m solution of phenyllithium in benzene. After 1 hour at −60° C., it is stirred for 16 hours at room temperature. The batch is acidified with glacial acetic acid and concentrated by evaporation. The residue is dispersed in ethyl acetate/water and the organic phase is washed, dried, filtered and concentrated by evaporation in succession with respectively saturated sodium bicarbonate and common salt solution. The residue is chromatographed on silica gel with methylene chloride: ethanol=10:1. The corresponding fractions are combined, concentrated by evaporation and recrystallized. 30 mg of 6-(1-isoquinolyloxy)-4-methoxymethyl-3-benzoyl-β-carboline of melting point 159°–160° C. (ethyl acetate/hexane) is obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of formula I

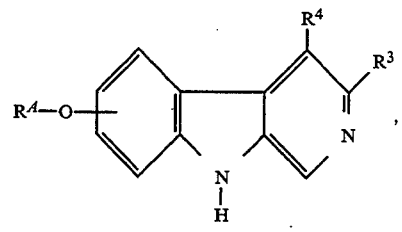

in which $R^A$ is an isoquinoline, quenoline, or quinoxaline, each optionally substituted with 1 or 2 of halogen, $C_{1-6}$ alkyl, $C_{1-6}$ alkoxy, $C_{1-6}$ alkylthio, trifluoromethyl or $SO_2$—$R^1$, $R^1$ is $C_{1-4}$ alkyl or phenyl optionally substituted 1–2 times with $C_{1-4}$ alkyl, wherein the substituent on $R^A$ is not halogen when $R^A$ is pyridine, $R^4$ is hydrogen, $C_{1-6}$ alkyl, $C_{1-6}$ alkoxy-$C_{1-2}$ alkyl, $R^3$ is —$CO_2$—$C_{1-6}$ alkyl, —$CO$-$R^2$, —$CO_2H$,

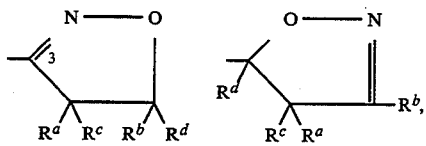

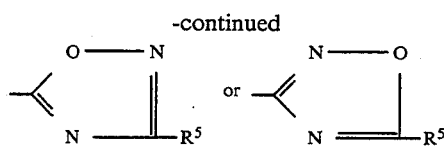

and

R² is C₁₋₄ alkyl, C₃₋₇ cycloalkyl, C₇₋₉ bicycloalkyl or a monocyclic or bicyclic C₆₋₁₂ aryl radical optionally substituted with C₁₋₄ alkyl, C₁₋₄ alkoxy or amino, Rᵃ and Rᵇ are the same or different and each is hydrogen, C₁₋₆ alkoxy, C₁₋₆ alkyl, —CH₂—C₁₋₄ alkyl, phenyl or benzyl, Rᶜ and Rᵈ each is hydrogen or together form a bond and R⁵ is hydrogen, C₁₋₄ alkyl or C₃₋₇ cycloalkyl, or an isomer thereof or an acid addition salt thereof.

2. 6-(1-Isoquinolyloxy)-4-methoxymethyl-β-carboline-3-carboxylic acid isopropyl ester, 6-(4-methyl-2-quinolyloxy)-4-methoxymethyl-β-carboline-3-carboxylic acid isopropyl ester, 6-(2-quinolyloxy)-4-methoxymethyl-β-carboline-3carboxylic acid isopropyl ester, 6-(3-chloro-2-quinoxalyloxy)-4-methoxymethyl-β-carboline-3-carboxylic acid isopropyl ester, 5-(2-isoquinolyloxy)-4-methoxymethyl-β-carboline-3-carboxylic acid isopropyl ester, 6-(1-isoquinolyloxy-4-methoxymethyl-3-benzoyl-β-carboline.

3. A compound of claim 1, wherein R⁴ is quinoline, isoquinoline or quinoxaline each optionally substituted with halogen, C₁₋₆ alkyl or C₁₋₆ alkoxy.

4. A compound of claim 1, wherein R³ is —CO₂—C₁₋₆ alkyl, —CO—R² wherein R² is a C₃₋₇ cycloalkyl or an optionally substituted phenyl radical or isoxazol-3-yl radical.

5. A pharmaceutical composition comprising an effective amount of a compound of claim 1 and a pharmaceutically acceptable carrier.

6. A method of treating epilepsy or anxiety in a patient in need thereof comprising administering an effective amount of a compound of claim 1.

* * * * *

UNITED STATES PATENT AND TRADEMARK OFFICE
CERTIFICATE OF CORRECTION

PATENT NO. : 5,348,958

DATED : September 20, 1994

INVENTOR(S) : Krüger, et al

It is certified that error appears in the above-indentified patent and that said Letters Patent is hereby corrected as shown below:

Claim 1, Column 10, Line 50: Delete "quenoline" and insert - - quinoline - -.

Claim 2, Column 12, Line 2: After "3" insert -- - --.

Signed and Sealed this

Sixth Day of December, 1994

Attest:

BRUCE LEHMAN

*Attesting Officer*  *Commissioner of Patents and Trademarks*